(12) United States Patent
Cauller

(10) Patent No.: US 7,630,771 B2
(45) Date of Patent: Dec. 8, 2009

(54) GROOVED ELECTRODE AND WIRELESS MICROTRANSPONDER SYSTEM

(75) Inventor: Lawrence James Cauller, Plano, TX (US)

(73) Assignee: MicroTransponder, Inc., Dallas, TX (US)

( * ) Notice: Subject to any disclaimer, the term of this patent is extended or adjusted under 35 U.S.C. 154(b) by 211 days.

(21) Appl. No.: 11/821,678

(22) Filed: Jun. 25, 2007

(65) Prior Publication Data

US 2008/0319506 A1    Dec. 25, 2008

(51) Int. Cl.
*A61N 1/375* (2006.01)

(52) U.S. Cl. ............................. 607/50; 607/2; 607/116

(58) Field of Classification Search .................. 600/377, 600/424; 606/129, 152; 607/1, 2, 60, 61, 607/116, 50; 128/903

See application file for complete search history.

(56) References Cited

U.S. PATENT DOCUMENTS

| | | | |
|---|---|---|---|
| 3,786,817 A | | 1/1974 | Palma |
| 3,955,560 A | | 5/1976 | Stein |
| 4,878,913 A | | 11/1989 | Aebischer |
| 4,940,065 A | | 7/1990 | Tanagho |
| 5,193,539 A | * | 3/1993 | Schulman et al. ............. 607/61 |
| 5,215,088 A | | 6/1993 | Normann |
| 5,312,439 A | * | 5/1994 | Loeb ............................. 607/2 |
| 5,358,475 A | | 10/1994 | Mares |
| 5,400,784 A | | 3/1995 | Durand |
| 5,510,628 A | | 4/1996 | Georger, Jr. |
| 5,524,338 A | | 6/1996 | Martyniuk |
| 5,735,863 A | | 4/1998 | Della Valle et al. |
| 5,833,603 A | | 11/1998 | Kovacs et al. |
| 5,925,053 A | | 7/1999 | Hadlock |
| 6,051,017 A | * | 4/2000 | Loeb et al. ..................... 607/1 |
| 6,456,866 B1 | * | 9/2002 | Tyler et al. .................. 600/377 |
| 6,505,075 B1 | | 1/2003 | Weiner |
| 6,587,725 B1 | | 7/2003 | Durand |
| 6,676,675 B2 | * | 1/2004 | Mallapragada et al. ...... 606/152 |
| 6,829,508 B2 | * | 12/2004 | Schulman et al. ........... 607/116 |

(Continued)

OTHER PUBLICATIONS

Kipke, Daryl R. et al., "Silicon-Substrate Intracortical Microelectrode Arrays for Long-Term Recording of Neuronal Spike Activity in Cerebral Cortex, IEEE Transactions on Neural Systems and Rehabilitation Engineering", Jun. 2003 vol. 11, No. 2., pp. 151-154.

(Continued)

*Primary Examiner*—Carl H Layno
*Assistant Examiner*—Luther G Behringer
(74) *Attorney, Agent, or Firm*—David C. Cain

(57) ABSTRACT

A grooved electrode adapted for interfacing cellular matter is provided. The grooved electrode includes grooves adapted for electrically interfacing the grooved electrode with cellular matter growing along the body of the grooved electrode. Further, the grooved electrode includes a wireless transponder adapted to electrically interface with cellular matter and to relay such interactions via RF signals. The RF signals received by the wireless transponder are modulated in response to electrical signals generated by the cellular matter, which are detected by the transponder. The grooved electrode may be implanted within peripheral nerves for treating various neurological conditions, which may include nerve rehabilitation and prosthetic actuation, severe pain, obstructive sleep apnea and so forth.

21 Claims, 6 Drawing Sheets

U.S. PATENT DOCUMENTS

| | | |
|---|---|---|
| 6,908,470 B2 | 6/2005 | Stieglitz |
| 7,001,608 B2 | 2/2006 | Fishman |
| 2002/0051806 A1* | 5/2002 | Mallapragada et al. ...... 424/423 |
| 2004/0059392 A1 | 3/2004 | Parramon |
| 2005/0137652 A1* | 6/2005 | Cauller et al. ................. 607/60 |
| 2007/0123938 A1* | 5/2007 | Haller et al. ................... 607/2 |

OTHER PUBLICATIONS

Vetter Rio J, et al., Chronic Neural Recording Using Silicon-Substrate Microelectrode Arrays Implanted in Cerebral Cortex, IEEE Transactions on Biomedical Engineering, Jun. 2004, vol. 51, No. 6, pp. 896-904.

* cited by examiner

GROOVED ELECTRODE AND WIRELESS MICROTRANSPONDER SYSTEM

BACKGROUND

Embodiments of the invention relate generally to systems and methods for interfacing cellular matter, particularly, to systems and methods facilitating signal communication between devices interfacing cellular matter and external systems.

BRIEF DESCRIPTION

A variety of medical conditions from which people may suffer involve disorders and/or diseases of neurological system(s) within the human body. Such disorders may include paralysis due to spinal cord injury, cerebral palsy, polio, sensory loss, sleep apnea, acute pain, and so forth. A characterizing feature of the aforementioned disorders and/or diseases may be, for example, the inability of the brain to neurologically communicate with neurological systems dispersed throughout the body. This may be due to physical disconnections within the neurological system of the body, and/or to chemical imbalances which may alter the ability of the neurological system to receive and/or transmit electrical signals, such as those propagating between neurons.

Advances in the medical field have produced techniques aimed at restoring or rehabilitating, to some extent, neurological deficiencies leading to some of the above-mentioned conditions. Further, such techniques may typically be aimed at treating the central nervous systems and, therefore, are quite invasive. This may include, for example, implanting devices, such as electrodes, into the brain and physically connecting, via wires, those devices to external systems adapted to send and/or receive signals to or from the implanted devices. In addition, the incorporation of foreign matter and/or objects into the human body may present various physiological complications, rendering such techniques very challenging to implement. For example, the size and extension of the implanted devices and wires extending therefrom may substantially restrict patient movement. Moreover, inevitable patient movement may cause the implanted device to dislodge within that portion of anatomy in which the device is implanted. This may result in patient discomfort and may lead to the inoperability of the implanted device, thus, depriving the patient from treatment. Consequently, this may require corrective invasive surgical procedures for repositioning the device within the body, thereby increasing risks of infection and/or other complications. In addition, an implanted device typically requires a built-in battery so that it can operate. If the device is to remain within the body for prolonged periods of time, such batteries are frequently replaced, requiring additional surgical procedures that could yet lead to more complications.

Hence, there is a need for implantable devices used with systems and/or methods adapted to address the aforementioned shortcomings.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
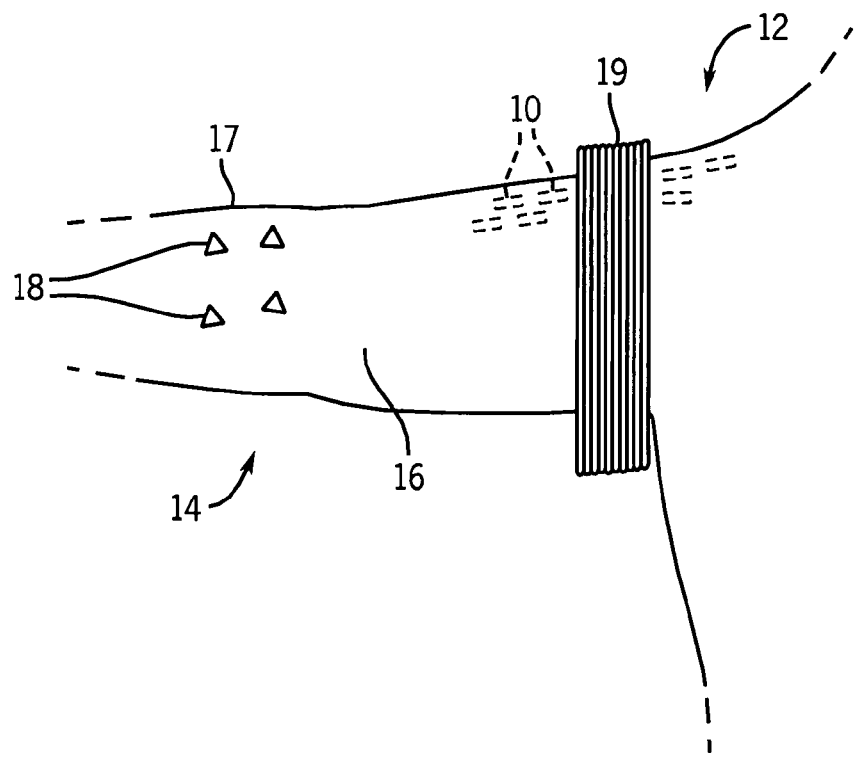
FIG. 1 illustrates a plurality of grooved electrodes implanted inside a human body, in accordance with an embodiment of the present technique.

Referring to FIG. 1, a grooved electrode 10 is shown as being implanted inside a human body 12, in accordance with an embodiment of the present technique. As will be described further below, the grooved electrode 10 is adapted to be implanted within the body 12 for interfacing cellular matter. In an exemplary embodiment, the grooved electrode 10 can be incorporated within the nervous system of the body 12, more particularly, within peripheral nerves of the nervous system. A peripheral nerve may be comprised of multiple nerve fibers, where each fiber includes one axon. Accordingly, the grooved electrode 10 may comprise biocompatible materials and/or components, enabling the grooved electrode 10 to assimilate and become part of the axons of the peripheral nervous system for extended periods of time. In addition, the grooved electrode 10 may be physically and/or chemically designed for promoting growth of cellular mater, such as axons of peripheral nerves, along portions of the grooved electrode 10 and/or in its vicinity. This enables the grooved electrode 10 to better mesh with the cellular mater, i.e., peripheral nerves, thereby enabling components of the grooved electrode 10 to optimally interact with the cellular matter. Further, by virtue of its adaptability to peripheral nerves, the grooved electrode 10 may be implanted within the body 12 using minimally invasive methods, thereby reducing risks of infections and/or other complications.

The grooved electrode 10 may include a wireless neuro-microtransponder (FIG. 4) configured to interact with certain portions of the peripheral nervous system. As will be discussed below, the wireless neuro-microtransponder incorporated within the grooved electrode 10 is adapted to convey signals, such as neurological signals, to or from the human body 12. In so doing, systems external to the body 12 may employ the grooved electrode 10 as an interface for detecting, transmitting or otherwise facilitating communication of electrical signals induced by various physiological processes occurring between various anatomical structures or communication of signals for actuating biomechanical devices.

For example, the grooved electrode 10 can be used with prosthetics for providing a neural interface between portions of the body 12 which are naturally anatomical and portions of the body 12 which may be artificial, such as artificial limbs. In FIG. 1, arm 14 may include a natural, i.e., non-prosthetic, portion 16 coupled to a prosthetic portion 17 adapted to act as an artificial extension of the arm 14. As further illustrated, a plurality of the grooved electrodes 10 may be disposed throughout portions 16 of the arm 14 and shoulder area of the body 12. As discussed further below, the grooved electrodes 10 can be used to wirelessly open neurological pathways between the brain and/or natural anatomical structures, such as between the portion 16 and the prosthetic 17. The prosthetic 17 may incorporate biomechanical devices 18 adapted to receive signals generated by peripheral nerves within portion 16 of the arm 14. The biomechanical devices 18 may include electromechanical devices some of which may be similar to the grooved electrode 10.

In this manner, the prosthetic 17 can be actuated with sufficient strength, dexterity and sensitivity, enabling a person to control the prosthetic 17 as if the prosthetic were a natural extension of the human body. It should be born in mind that while the illustrated embodiment may show the grooved electrodes 10 as being disposed within the arm 14 for accommodating prosthetic movements, other embodiments may incorporate the grooved electrodes 10 in other portions of the body 12 for other purposes. For example, the grooved electrode 10 may be used to treat patients suffering from obstructive sleep apnea. In such instances, the grooved electrodes 10 may be implanted within the head of the body 12, specifically, within nerves controlling muscles of the soft palate around the base of the tongue. For example, the grooved electrode 10 may be used to electrically stimulate a hypoglossal nerve so as to prevent the aforementioned muscles from obstructing breathing airways of the patient. Still in other instances, the grooved electrodes 10 may be used to treat patients suffering of persistent and/or acute pain by stimulating the peripheral nerves to cause paresthesia of an area where pain is felt.

As mentioned, the plurality of grooved electrodes 10, such as those disposed within the portion 16 of the arm 14, may be employed as a neurological interface enabling neurological signals to propagate throughout anatomical regions of the body 12 whose neurological pathways are compromised or are otherwise absent. To optimize the grooved electrode 10 for use within the nervous system of the body 12, those skilled in the art will appreciate the importance in choosing proper tissue sites within which to incorporate the grooved electrode 10. For example, peripheral nerves may include fiber pathways that play an important role in propagating neurological signals, such as those needed to control the prosthetic portion 17 of the arm 14. To accommodate such attributes, grooved electrodes 10 may specifically be designed and configured to mechanically and electrically interface with such peripheral nerves. For example, each of the grooved electrodes 10 may be smaller than 1 millimeter, and each may be adapted to detect axonal spike signals, whose magnitudes are as low as 10 microvolts. To detect such minute signals, the grooved electrode 10 may include, for example, bio-synthetic nerve guides with electrically sensitive carbon nanotubes adaptable to pick up weak electrical spike signals generated by individual peripheral nerve axons. Further, the grooved electrode 10 may include neurotrophic factors adapted for promoting growth and fusion of axons within a mesh of carbon nanotubes disposed within a nerve guide leading to components of the grooved electrode.

To establish wireless neurological pathways, each of the grooved electrodes 10 incorporates a wireless neuro-microtransponder enabling each of the grooved electrodes 10 to receive and transmit signals to or from the body 12. In the illustrated embodiment, a coil 19 may be disposed about portions of body 12, particularly, about those portions in which the grooved electrodes are implanted for facilitating wireless communication between the grooved electrode 10 and external systems. The coil 19 is adapted to generate electromagnetic signals, such as radio frequency (RF) signals, which can be intercepted by various circuit components of the transponder. As discussed further below, such circuit components are adapted to modulate the received RF signals in response to electrical signals generated by the peripheral nerves detected by the grooved electrode 10. In other words, electrical interactions of the transponder with the peripheral nerves manifest as unique modulations in the RF signals generated by the coil 19. These modulations are detected by the coil 19 and, thereafter, undergo further signal processing for identifying the extent and location of the neurological activity within those portions of the body 12 where the grooved electrodes 10 are implanted. In an exemplary embodiment, the grooved electrodes 10 may sense neurological signals, such as those propagating from the brain via the hand 14, aimed at moving the prosthetic 17. Accordingly, the transponder senses such signals and, in so doing, modulates the RF signals generated by the coil 19. The coil 19 receives the modulated RF signals, which could then be analyzed to determine the nature of the desired movement. Thereafter, the coil 19 may generate RF signals for actuating the biomechanical devices 18, thereby enabling the prosthetic 17 to move according to the desired movements.

Further, the RF signals generated by the coil 19 are further adapted to power the transponder of the grooved electrode 10, thereby eliminating the incorporation of power supplies, i.e., batteries, within the grooved electrode 10. This may simplify electrical transponder circuitry, which could promote the miniaturization of the grooved electrode 10 and components thereof. This may further enable clinicians to implant the grooved electrode 10 within the body 12 with relative ease and accuracy. In addition, the ability to RF power the grooved electrode 10 may prevent patients from undergoing repetitive invasive surgical procedures needed for replacing batteries, such as those used in existing systems.

Hence, each of the grooved electrodes 10 may form a single autonomous wireless unit adapted to independently interact with peripheral nerves, as well as with other grooved electrodes and/or other systems disposed in its vicinity. The wireless feature of the grooved electrodes 10 may replace wire-coupled systems, thereby unrestricting patient movement.

Figure 2:
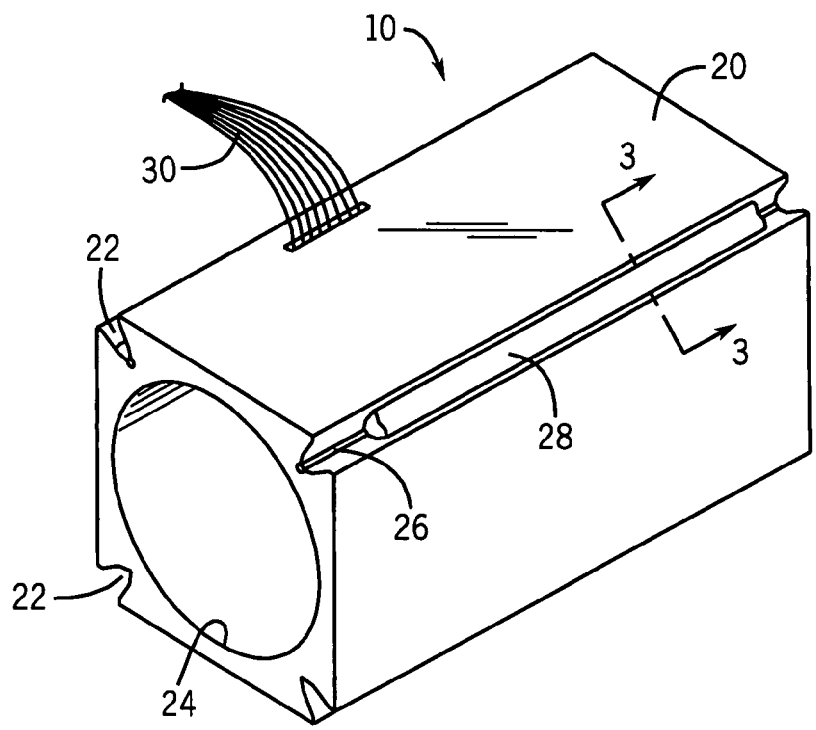
FIG. 2 is a perspective view of a grooved electrode, in accordance with an embodiment of the present technique.

FIG. 2 is a perspective view of the grooved electrode 10, in accordance with an embodiment of the present technique. In the illustrated embodiment, the grooved electrode 10 includes a hollow elongated rectangular body 20 forming an encasement through which electronic components can be inserted and housed. The body 20 has grooves 22 extending lengthwise throughout the body 20. The grooves 22 are adapted to facilitate growth of cellular matter, i.e., peripheral nerves, about the exterior portions of the grooved electrode 10. To facilitate optimal cellular growth, the grooved electrode 10 may be shaped to have certain geometrical features and characteristics corresponding to those portions of anatomies in which the grooved electrode 10 is implanted. For example, to facilitate the growth of peripheral nerves, the grooved electrode 10 may be shaped to have a length of less than two millimeters with the width and the height being much smaller than its length. Such dimensional characteristics of the grooved electrode 10 may correspond to the length of an active current zone generated during a peak spike phase of an active nerve fiber, as may be appreciated to those skilled in the art. In accordance with the present technique, this enables the grooved electrode 10 to have sufficient contact with peripheral nerve fibers growing along the grooved electrode 10, thereby providing robust signal-sampling capabilities during the peak spike phase of the nerves. It should be appreciated that the grooved electrode 10 may attain shapes and sizes other than the one illustrated by FIG. 1, such as those for accommodating implantation of the groove electrode through various portions of the body 12 (FIG. 1).

Further, the body 20 of the grooved electrode 10 may be formed of a biocompatible polymer adapted to seal and insulate components and/or devices, i.e., transponder (FIG. 4), encased within the body 20. Such a polymer may include FDA-approved polymer materials, such as polymethylmethacrylate (PMMA), polydimethylsiloxane (PDMS), polytetraflouroethylene (PTFE), parylene, as well as biocompatible forms of polyurethane or polycarbonate. These and other envisioned materials from which the body 20 may be made are adapted to promote growth and fusion of axons along the exterior portions of the grooved electrode 10.

As further illustrated, the grooved electrode 10 includes an opening 24 disposed at one of the body 20 through which the microtransponder (FIG. 4) is fitted. Once peripheral nerve fibers grow lengthwise along the grooves 22, a configuration is achieved whereby the peripheral nerves encase the transponder disposed within the body 20. Further, electrode leads 26 disposed along the grooves 22 are adapted to electrically connect axons of the peripheral nerves growing along the grooves 22 with the transponder encased within the body 20. In this manner, the transponder may form an interface capable of sensing or stimulating those axons disposed directly in the vicinity of the groove electrode 10. In addition, the grooved electrode 10 may be coupled to wire leads 30, configured to electrically couple the grooved electrode 10 to external devices, such as other grooved electrodes. Accordingly, the wire leads 30 may be adapted for delivering power to components disposed within the grooved electrode. The wire leads 30 are also adapted to transfer electrical signals, such as those generated by neurons, or those used for stimulating the neurons of a peripheral nerve. In other exemplary embodiments, the aforementioned functionalities could also be achieved by using wireless techniques, as explained further below.

Figure 3:
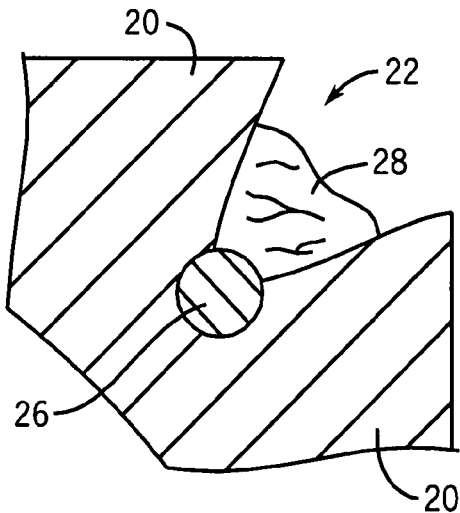
FIG. 3 is a front cross sectional view of a portion of the grooved electrode shown in FIG. 2, in accordance with an embodiment of the present technique.

To optimize the interface between the peripheral nerves and components disposed within the grooved electrode 10, the grooves 22 may be carved throughout four edges of the grooved electrode 10. As shown in FIG. 3, which is a front cross-section of FIG. 2 taken along line 3-3, each of the grooves 22 and the body 20 houses the electrode lead 26, which extends lengthwise along the grooves 22. As further illustrated, the electrode lead 26 may be embedded within the body 20 such that a portion of the electrode 26 may be fully engulfed by the body 20, while a remaining portion of the electrode lead 26 may be exposed to an opening formed by the groove 22. The electrode leads 26 are adapted to contact those axons 28 growing along the opening of the grooves 22, thereby forming an electrical connection between the axons and contact leads of a neural micro-transponder disposed within the grooved electrode 10. This electrical connection permits electrical current to flow between the neural axons 28 and the transponder as, for example, may occur during detection of spike signals. In an exemplary embodiment, electrode leads 26 may be made from conductive carbon nanotube or other nano-scale structures having neurotrophic properties.

In other embodiments, electrode leads 26 may be made from electrically conductive, biocompatible and corrosion-resistant materials including metallic alloys, such as medical-grade stainless steel, gold, platinum and/or a combination thereof. Other suitable materials from which the electrode leads 26 may be formed include inert-non-metallic conductors, such as graphite or polymer composites.

As illustrated by FIG. 3, the grooves 22 are carved along the body 20 in a manner permitting proper growth of the axons 28 lengthwise within the groove along the exterior portions of the grooved electrode 10. In addition, to promote suitable electrical contacts between the axons 28 and the electrode leads 26, the grooves 22 may be shaped to have certain dimensional characteristics. For example, the grooves 22 may be carved so as to permit healthy maturation of at least one nerve fiber. At the same time, the grooves 22 may be carved to be small enough for minimizing the number of fibers exposed to the electrode lead 26. In an exemplary embodiment, the aforementioned attributes may be achieved by fabricating the grooves 22 to be approximately 10 micrometers in depth and width.

As further illustrated by FIG. 3, the opening defined by each of the grooves 22 may be shaped to have a unique profile. For example, the opening of the groove 22 may be profiled to have a U, V, or rectangular shape. For example, the illustrated V-shaped profile may render the opening of each of the grooves 22 to be approximately 15 micrometers wide, tapering down to approximately 5 micrometers at the exposed electrode surface at the floor or fundus of the groove. It should be born in mind that the openings of the grooves 22 may be shaped to accommodate varying needs, as prescribed by physiological, anatomical and/or clinical constraints.

Further, in accordance with the above mentioned characteristics and profiles of grooves 22, the grooved electrode 10 may be configured to optimally contact and stimulate individual nerve fibers which grow along the grooves 22. Particularly, the above mentioned design of the grooves 22 is adapted to permit unrestrained fiber growth, thereby eliminating risks of long term fiber damage, such as those that are associated with existing 'sieve' designs. Further, the grooves 22 are adapted to isolate fewer fibers which make contact with each electrode lead 26, thereby providing finer stimulus resolution and more discrete detection of fiber activity. In addition, the groove may be filled with neurotrophic factors or other biochemicals 28 that guide or otherwise facilitate fiber growth in direct contact with the conductive electrode surface 26 along recessed portions forming the floor of the groove.

Figure 4:
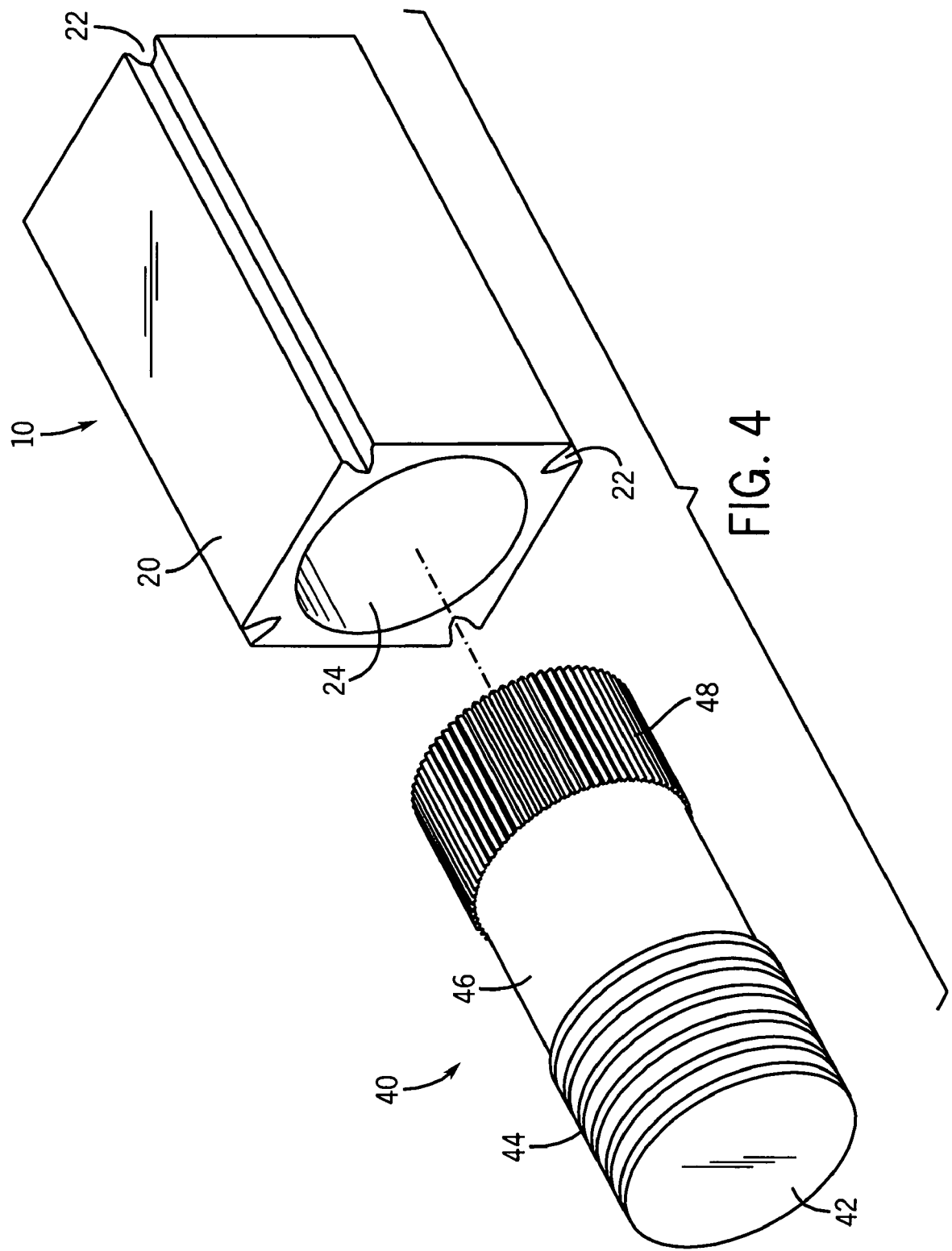
FIG. 4 is an exploded perspective view of a grooved electrode fitted with a neuro-microtransponder, in accordance with an embodiment of the present technique.

FIG. 4 is an exploded perspective view of the grooved electrode 10 fitted with a wireless neuro-microtransponder 40, in accordance with an embodiment of the present technique. As illustrated, the transponder 40 is adapted to fit within the grooved electrode 10 through the opening 24. The transponder 40 may be inserted within the grooved electrode 10 together with slow releasing neurotrophic substances and anti-inflammatory gels for minimizing aversive tissue reactions and for promoting the proper implantation of the grooved electrode 10 within the body. In this manner, the grooved electrode 10 and the transponder 40 make up a module adapted to physically, electrically and chemically interact with peripheral nerves located in the vicinity of the grooved electrode 10. Specifically, axons of peripheral nerves growing along exterior portions of the grooved electrode 10, as facilitated by the grooves 22, may electrically interface with the transponder 40 via the electrode leads 26. This configuration enables signals to propagate between the transponder 40 and peripheral nerves. Further, the transponder 40 includes wireless components adapted to communicate with systems external to the body, thereby enabling such systems to transmit and receive signals to or from the peripheral nerves within the body in which the grooved electrode is implanted.

The transponder 40 includes a magnetic core 42 about which microcoils 44 are coiled. The microcoils 44 form an inductor adapted to magnetically interact with electromagnetic fields, such as those propagating from sources external to the grooved electrode 10. In this manner, the microcoils 44 enable the transponder 40 to receive and/or transmit signals from or to the external systems with which the transponder 40 communicates. In addition, the microcoils 44 are adapted to power the transponder 40 through power induction. In other words, the microcoils 44 are adapted to received RF signals and convert those into electrical signals used to electrically power components of the transponder 40. In this manner, the transponder 40 may operate while being battery-free for extended periods of time.

The coil cores 42 may be fabricated out of nano-crystalline magnetic alloys, adapted for achieving a high inductance (L) at radio frequencies. In the illustrated embodiment, the coils 44 may have an (L) value four orders of magnitude greater than (L) values achieved by inductors formed of conventional materials. Further, each coil of the coils 44 may be fabricated to have a diameter that is as small as 100 micrometers, thereby producing an inductance of approximately 10 nano-Henry. The coil cores 42 may be fabricated using laser machining methods of nano-crystalline materials, such as cobalt. Fabrication of the coils 44 may also involve employing techniques used in production of micro-electromechanical systems (MEMS) and nano-electromechanical systems (NEMS).

The transponder 40 further includes a portion 46 adapted to encapsulate circuitry of the microtransponder. The portion 46 also includes contact leads which connect between the circuitry the grooved electrodes 10. As will be discussed further below, the circuitry encapsulated by the portion 46 includes electrical components adapted to sense and/or stimulate the peripheral nerves interfacing with the grooved electrode 10. For example, the circuitry 46 includes identification (ID) circuitry adapted to generate unique RF signals in response to the neural spike signals generated by the peripheral nerves. This RFID capability of the transponder 40 is configured to relay neurological activity occurring within the body to systems external to the body. The ID information may also be used to distinguish between a plurality of transponders emitting RF signals simultaneously from their respective grooved electrodes implanted within the body 12, as shown in FIG. 1.

Further, the portion 46 may be coated with conductive materials, such as gold or other biocompatible conductors, to form the electrical connection between the circuitry encapsulated by the portion 46 and the electrode leads 26 disposed within the grooves 22 of the grooved electrode 10. The transponder 40 further includes a capacitor 48 disposed at the rear portion of the transponder 40. The capacitor 48 may be made from a plurality of nano-tube super capacitors, adapted to increase the capacitance (C) of the transponder 40. The capacitor 48 and the inductor 44 form an LC circuit adapted to modulate received RF signals for producing the RFID signal of the transponder 40.

Figure 5:
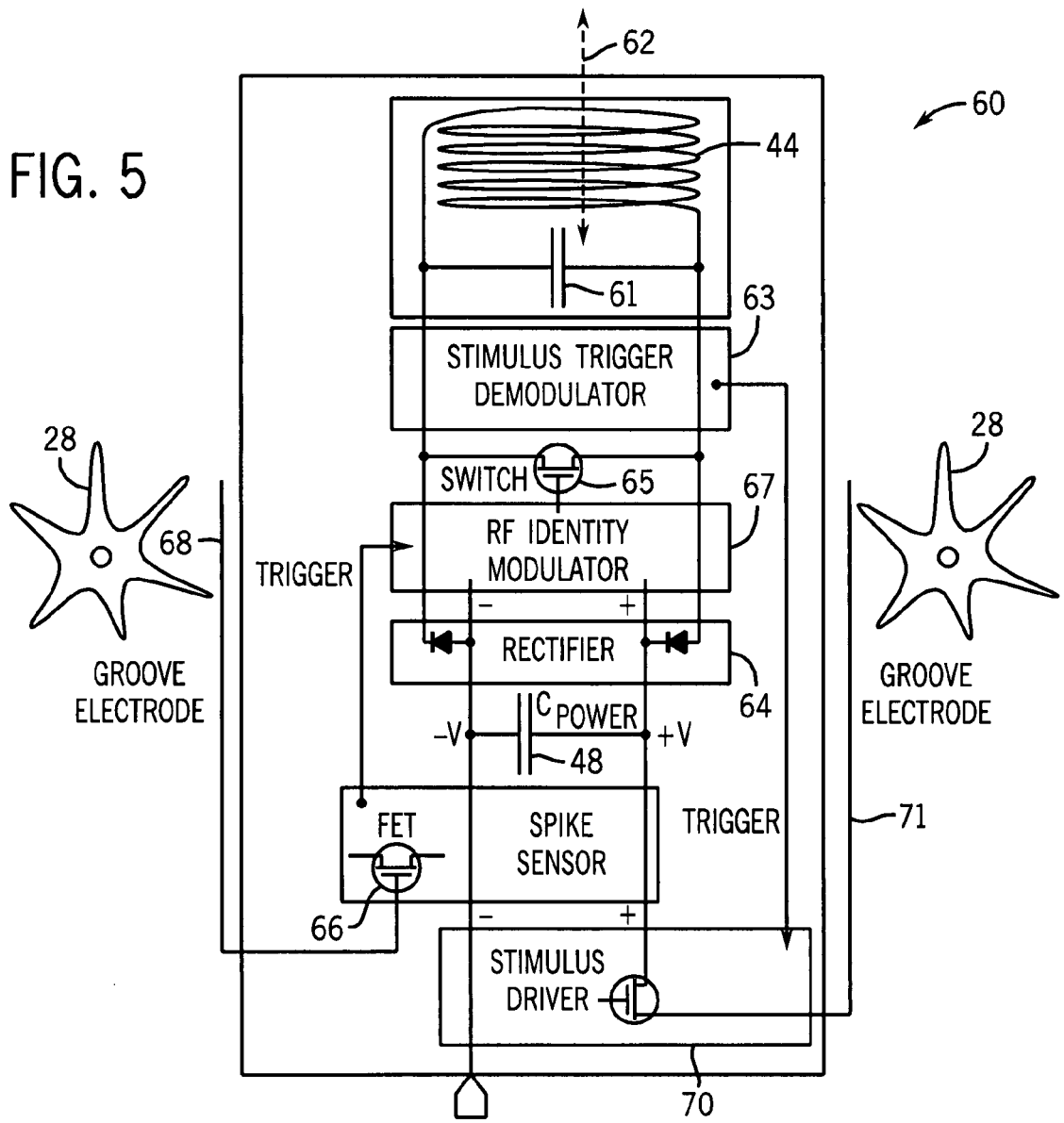
FIG. 5 is a schematic circuit diagram of the neuro-microtransponder, in accordance with an embodiment of the present technique.

FIG. 5 is a schematic diagram of a circuit 60 disposed within the neuro-microtransponder 40, in accordance with an embodiment of the present technique. The circuit 60 includes electrical components adapted to electrically interface with neurons of peripheral nerves, such as those disposed along the grooves 22 of the grooved electrode 10, discussed hereinabove with relation to FIGS. 2-3. The circuit 60 further includes electrical components which enable the transponder 40 to wirelessly interact with systems external to the transponder 40. Such systems may include other transponders implanted within the body or external coils and/or a receiver, such as those shown in FIGS. 1 and 6, respectively. The wireless capabilities of the circuit 60 enable the delivery of electrical signals to or from the peripheral nerves. These include electrical signals indicative of neural spike signals and/or signals configured to stimulate the peripheral nerves.

Accordingly, the circuit 60 includes the coils 44 coiled about a central axis 62. The coil 44 is coupled in parallel to a capacitor 61 and to a stimulus trigger demodulator 63, which in turn is coupled to an RF identity modulator 67 via a switch 65. Further, the RF identity modulator 67 is coupled to a rectifier 64, which in turn is coupled to a spike sensor 66 and to a stimulus drive 70. The rectifier 64 and the spike sensor 66 are both coupled in parallel to a capacitor 48. In addition, the spike sensor 66 is coupled to contact leads 68, thereby electrically connecting the spike sensor 66 to the axon 28. Similarly, contact lead 71 connects the stimulus driver 70 to the neuron 28. The spike sensor 66 is made up of one or more field effect transistors (FET). As will be appreciated by those of ordinary skilled in the art, the FET may include metal oxide semiconductors field effect transistors (MOSFETS), such as those fabricated using standard small scale or very large scale integration (VLSI) methods. Further, the spike sensor 66 is coupled the RF identity modulator 67, which is adapted to modulate an in coming/carrier RF signal in response to neural spike signals detected by the spike sensor 66. The contact leads 68 and 71 to which the sensor 66 and the stimulus driver 70 are connected, respectively, may be part of the portion 46 (FIG. 4), adapted to interface with the axon 28 of the peripheral nerve disposed along the grooved electrode 10 (FIG. 2).

One configuration of the above components depicted by FIG. 5 enables the neuro-microtransponder 40 to operate as an autonomous wireless unit, capable of detecting spike signals generated by peripheral nerves, and relaying such signals to external receivers for further processing. It should be born in mind that the transponder 40 performs such operations while being powered by the external RF signals. The above mentioned capabilities are facilitated by the fact that magnetic fields are not readily attenuated by human tissue. This enables the RF signals to sufficiently penetrate the human body so that signals can be received and/or transmitted by the transponder 40. In other words, the microcoils 44 are adapted to magnetically interact with the RF field whose magnetic flux fluctuates within the space encompassed by the coils 44. By virtue of being an inductor, the coils 44 convert the fluctuations of the magnetic flux of the external RF field into alternating electrical current, flowing within the coils 44 and the circuit 60. The alternating current is routed, for example, via the coils 44 into the rectifier 64, adapted to convert the alternating current into direct current. The direct current may then be used to charge the capacitor 48, thereby creating a potential difference across the FET of the sensor trigger 66.

In an exemplary embodiment, a gate of the FET 66 may be coupled via a contact lead 68 to the neuron 28. The gate of the FET may be chosen to have a threshold voltage that is within a voltage range of those signals produced by the neural axons. In this manner, during spike phases of the neural axons, the gate of the FET 66 becomes open, thereby closing the circuit 60. Once the circuit 60 closes, the external RF field, the inductor 44 and the capacitor 48 induce an LC response, which modulates the external RF field with a unique modulating frequency. The LC characteristic of the circuit 60, as well as the threshold voltage of the gate of FET 66, can be chosen to determine the unique modulation, thereby providing a desired ID signal for the transponder 40. Accordingly, the FET 66 provides the RF identity modulator 67 with a trigger signal for generating desired RF signal. The ID signal may indicate the nature of the neural activity in the vicinity of the transponder 40, as well as the location of the neural activity within the body. It should be appreciated that the RF capabilities, as discussed above with respect to the circuit 60, render the neuro-microtransponder a passive device which reacts to incoming carrier RF signals. That is, the circuit 60 does not actively emit any signals, but rather reflects and/or scatters the electromagnetic signals of the carrier RF wave to provide signals having specific modulation. In so doing, the circuit 60 draws power from the carrier RF wave for powering the electrical components forming the circuit 60.

While the above-mentioned components illustrated in FIG. 5 may be used to receive signals from the transponder 40 (FIG. 4) in response to spike signals generated by peripheral nerves, other components of the circuit 60 of the transponder 40 may include components for stimulating the peripheral nerves using the external RF signals. For example, the RF signals received by the coils 44 may be converted to electrical signals, via the stimulus trigger modulator 63, so as for providing sufficient current and voltage for stimulating the peripheral nerves. Hence, the stimulus trigger demodulator 63 derives power form an RF carrier signal for powering the stimulus driver 70, which delivers electrical signals suitable for stimulating the axons 28. This may be used to treat nerves that are damaged or that are otherwise physiologically deficient.

Figure 6:
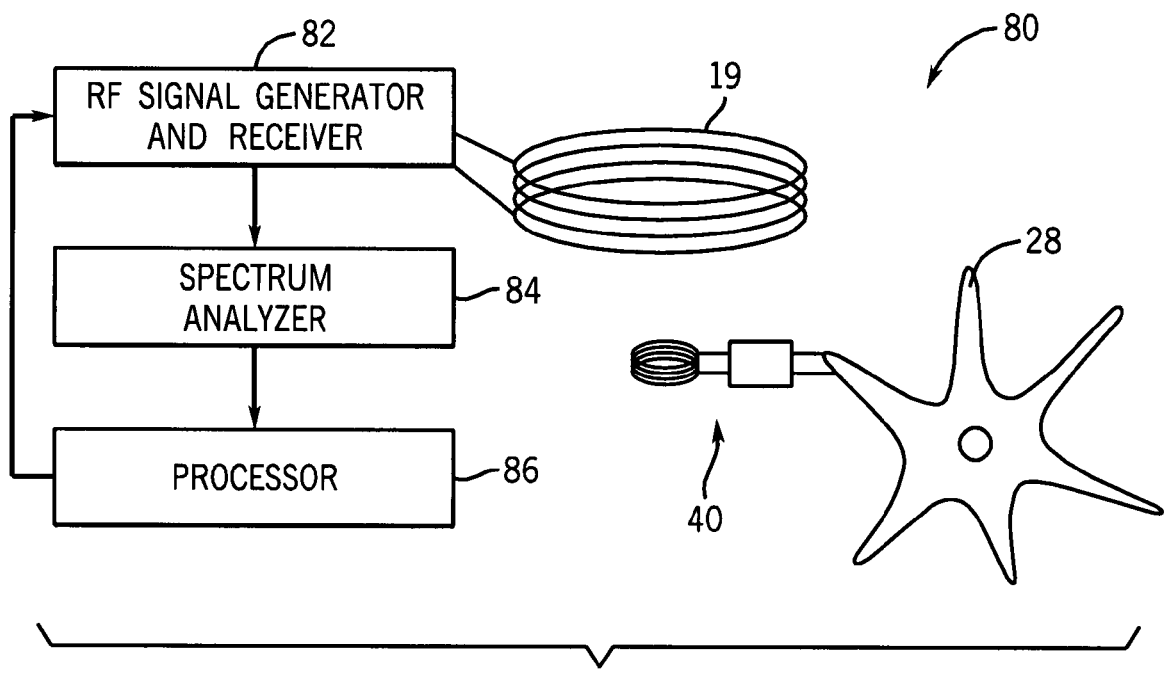
FIG. 6 is a schematic diagram illustrating the manner of operation of the neuro-microtransponder, in accordance with an embodiment of the of the present technique.

FIG. 6 is a schematic diagram of a system 80 used for interfacing cellular matter, in accordance with an embodiment of the present technique. The system 80 is adapted to wirelessly interface with cellular matter, such as peripheral nerves. The system 80 is further adapted to receive signals, such as neural spike signals, generated by the peripheral nerves, and analyze those signals to provide feedback and/or treatment to other biological and/or biomechanical systems to which the system 80 is additionally coupled. In the illustrated embodiment, the system 80 includes the neuro-microtransponder 40 interfacing with cellular matter, such as the neuron 28 of a peripheral nerve, in a manner described and illustrated hereinabove and shown in FIGS. 1-5. While the present exemplary embodiments may show the single transponder 40 coupled to the neuron 28, other embodiments may include the transponder 40 coupled to more than a single neuron and/or a plurality transponders coupled to a plurality of neurons, some of which may or may not be in close proximity to one another.

The system 80 further includes the coil 19 disposed in the vicinity of the transponder 40 and the neuron 28. The coil 19 is coupled to an RF signal generator and receiver (RFGRC) 82, which is coupled to a spectrum analyzer 84. The spectrum analyzer 84 is coupled to a processor 86, which is also coupled to the RFGRC 82. The RFGRC 82 provides and external RF signal, such as 100 MHz, for powering the transponder 40 and for enabling the transponder 40 to modulate the external RF signal so as to produce an ID signal. In an exemplary embodiment, the modulation frequency produced by the transponder 40 may be two orders of magnitude less than the original RF signal, however, this may vary depending on the type of cellular matter interfaced and the type of transponders used. In embodiments where a plurality of transponders may be employed, a modulation frequency of approximately 1 MHz provides a relatively high bandwidth for the ID signal. This enables the system 80 to distinguish between relatively large amounts of neural-microtransponders responding to electrical neural signals, some of which may be closely coincident.

Further, the RFGRC 82 receives the modulated RF signal and forwards the signal to the spectrum analyzer 84 for analysis. The spectrum analyzer is adapted to determine the modulation frequency, which is then provided to the processor 86 adapted to determine the ID signal characteristic of the spike signal detected by the transponder 40. In response to the identified spike signals, the processor 86 may prompt the RFGRC 82 to generate RF signals adapted to stimulate other biological and/or biomechanical systems to which additional transponders may be coupled. For example, the modulated RF signal received by the RFGRC 82 may originate from neural spike signals generated by peripheral nerves that are severed or are otherwise damaged. In response to such signals, the processor 86 may prompt the RFGRC 82 to actuate biomechanical devices, such as those incorporated into prosthetics, thereby inducing movement. The capabilities provided by the system 80 for interfacing cellular matter also facilitate treatment of various neurological conditions some of which may include acute pain and obstructive sleep apnea.

Further, in another exemplary embodiment, the configuration provided by the system 80 may be adapted to generate load modulation in the transponder 40 by switching the drain-source resistance of the FET of the circuit 60. This configures the circuit 60 to function as a designed to detect the carrier signal. As mentioned above, in other embodiment the system 80 may be used for stimulating the peripheral nerves. Hence, the carrier wave emitted by the external coil 19 may provide the transponder 40 with power for triggering electrodes adapted to deliver electrical signals to the peripheral nerves. In this mode of operation, the powering of the transponder 40 and, thereafter, the stimulation of the peripheral nerves may occur in a periodic sequence in accordance with a specific frequency.

Figure 7:
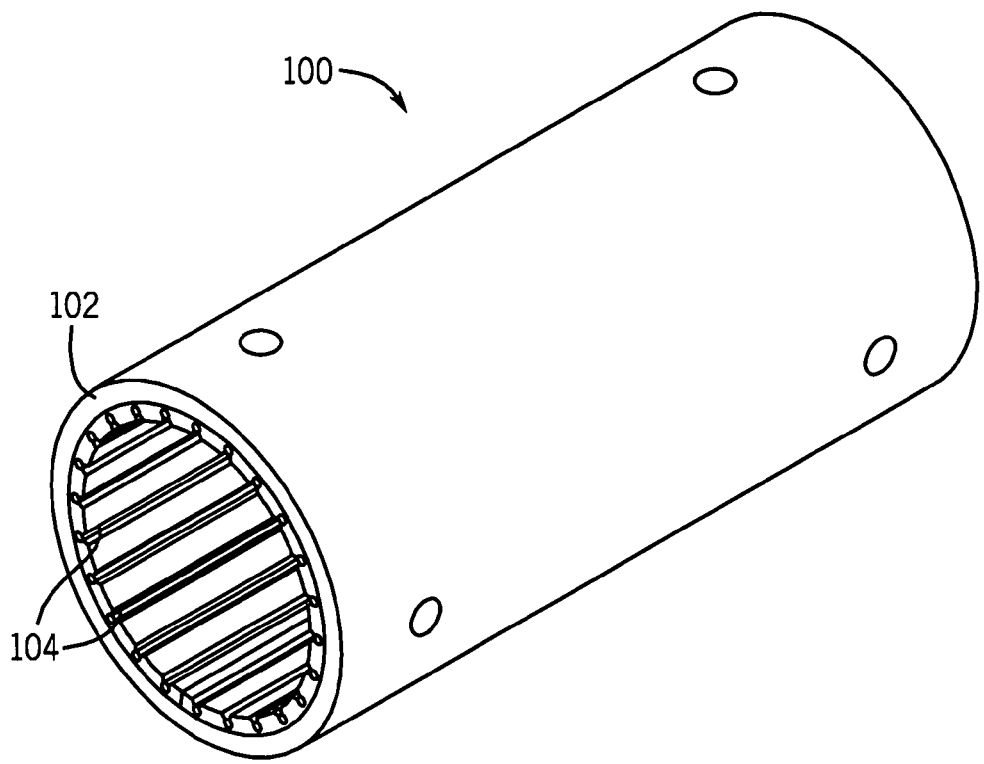
FIG. 7 is a perspective view of another embodiment of grooved electrodes, in accordance with the present technique.
Figure 8:
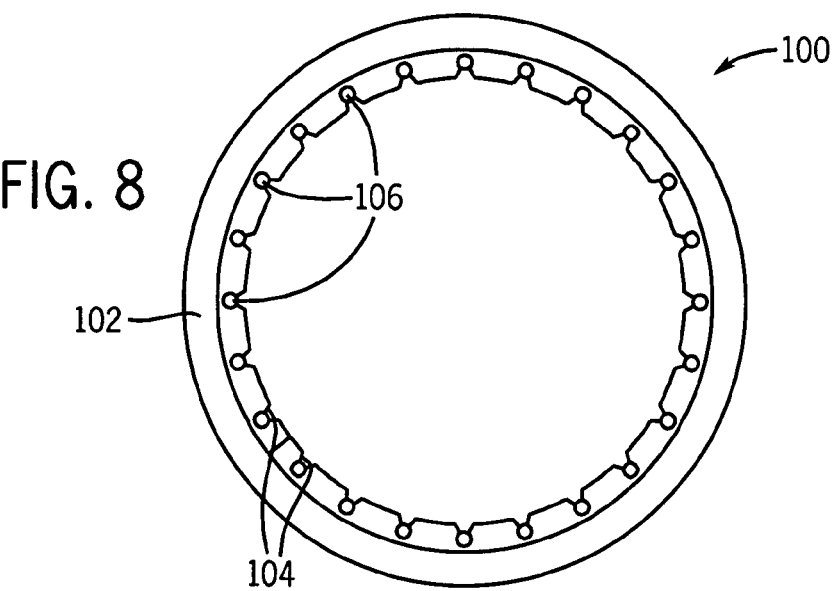
FIG. 8 is a front view of the grooved electrodes shown in FIG. 7.

FIGS. 7 and 8 are perspective and front views, respectively, of another exemplary embodiment of grooved electrodes, in accordance with the present technique. Accordingly, grooved electrode 100 may be made up from a substrate 102 conformed to a hollow cylinder populated with grooves 104 extending lengthwise along the interior portion of the cylinder. As illustrated by FIG. 8, grooved electrode 100 includes electrode leads 106 having a diameter less than 50 micrometers, disposed within the grooves 102. Similar to the electrode leads 26 discussed above, the electrodes 106 are adapted to contact axons growing along the grooves 22, thereby forming an electrical connection between the axons and neural microtransponders which may be exterior to the grooved electrode 100. The electrode leads 106 may be made from conductive carbon nanotubes, having neurotrophic properties, or from electrically conductive, biocompatible and corrosion-resistant materials including metallic alloys. Such alloys may include medical-grade stainless steel, gold, platinum and/or a combination thereof. Other suitable materials from which the electrode 106 may be formed include inert-non-metallic conductors such as graphite or polymer composites.

The grooved electrode 100 can be constructed by initially embedding a layer of the electrodes 106 within a pre-folded flat substrate 102 formed by casting a biocompatible polymer, such as sylgard. Thereafter, the grooves 104 are carved through the substrate 102, thereby exposing a portion of each the electrode leads 106, as illustrated in FIG. 8. Thereafter, the substrate 102 is rolled into a cylindrical structure forming the grooved electrode 100. This configuration enables neural fibers to grow and fuse with the interior portions of the grooved electrode 100. To maximize likelihood that the fibers growing along the grooves 104 properly contact the electrode leads 106, the grooves 104 may be filled with biochemical factors promoting fiber growth along the grooved electrode 100, as well as adhesion thereto. The cylindrical structure provided by the grooved electrode 100 can further facilitate formation of artificial fascicles which otherwise form internal structures of peripheral nerves, as appreciated to those skilled in the art.

Figure 9:
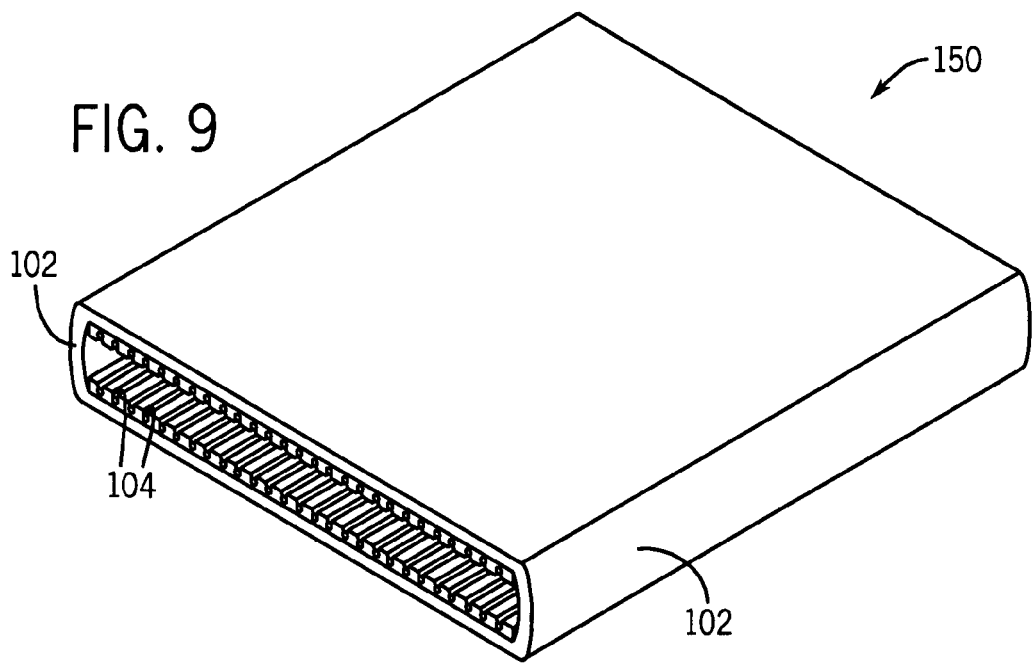
FIG. 9 is a perspective view of another configuration showing grooved electrodes, in accordance with an embodiment of the present technique.
Figure 10:
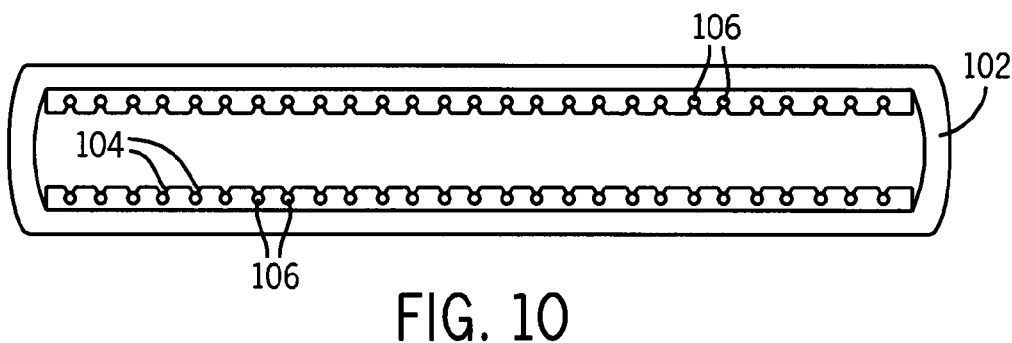
FIG. 10 is a front view of the configuration shown in FIG. 9, in accordance with an embodiment of the present technique.

FIGS. 9 and 10 are perspective and front views, respectively, of another exemplary embodiment of grooved electrodes, in accordance with the present technique. Accordingly, grooved electrode 150 is similar to the grooved electrode 100 discussed hereinabove in that both grooved electrodes 100, 150 may be formed using similar materials and techniques. The grooved electrode 150 is fabricated to form a flattened structure that avoids structural failures which otherwise may result from rolling or flexing the substrate 102. The flattened structure of the grooved electrode 150 may be used to force the fibers in fascicles to grow in contact with the electrode 106. This may be done, for example, by flattening the grooved electrode 150 to a thickness less than the fascicles, e.g., <0.3 millimeter.

Similarly, other embodiments may include grooved electrodes having various shapes and configurations adapted to promote growth of cellular matter along the body of the grooved electrodes. For example, rather than disposing electrodes, such as the electrode 106, along the interior volume of the grooved electrodes (FIGS. 7-10), the electrodes 106 can be disposed along exterior portions of the grooved electrodes. Such exemplary embodiments may correspond to, for example, folding the substrate 102 so that the grooves 104 face outward. Thus, the grooves can promote growth of peripheral nerves along the outer portions of the grooved electrode. In addition, this configuration may be implemented to produce grooved electrodes having other geometrical shapes, such as of the grooved electrodes shown in FIGS. 9 and 10.

Figure 11:
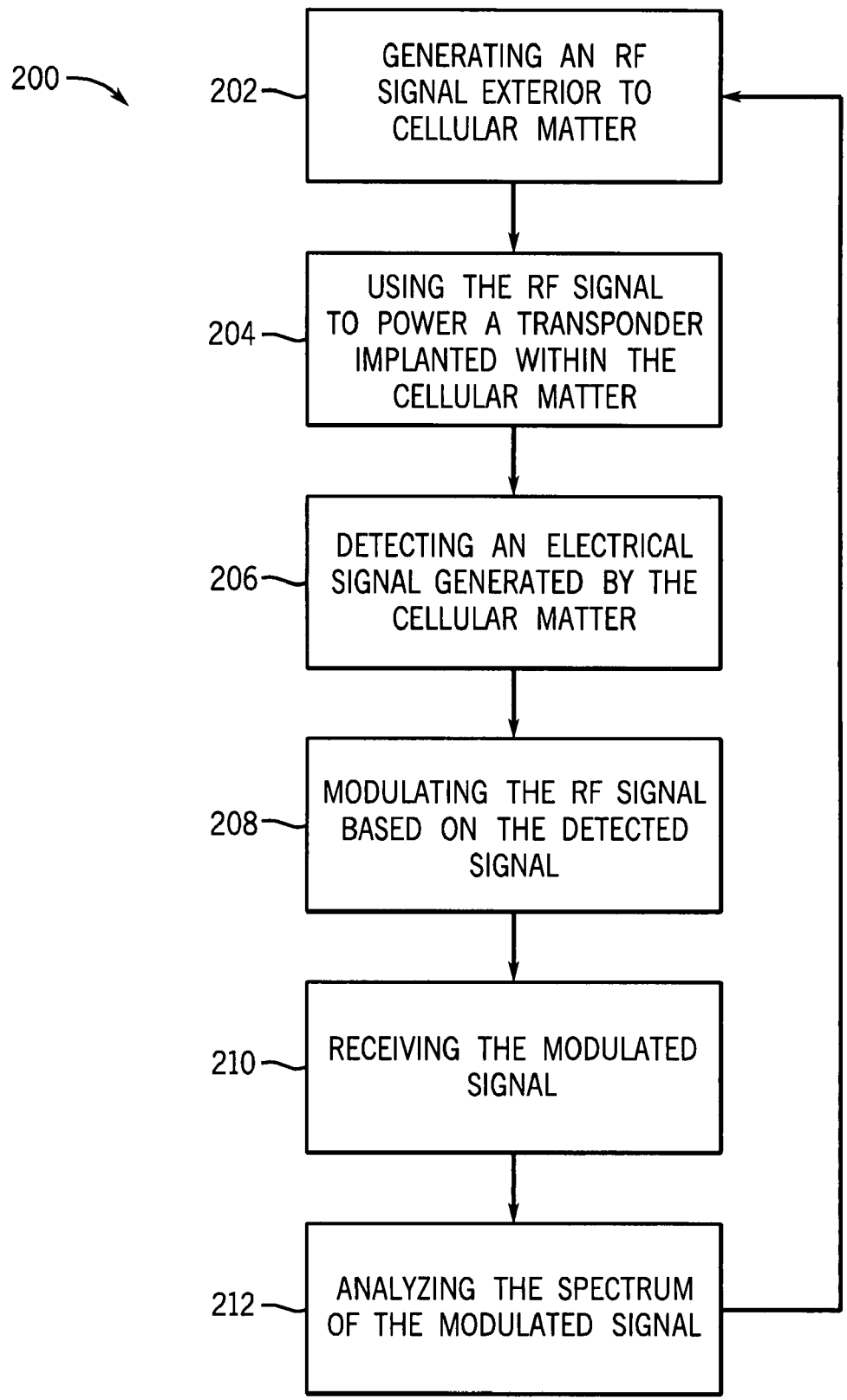
FIG. 11 is block diagram of a method for interfacing cellular matter, in accordance with an embodiment of the present technique.

FIG. 11 is a block diagram of a method 200 for interfacing cellular matter, in accordance with an embodiment of the present technique. The method 200 may be used to wirelessly interface peripheral nerves using devices, such as the grooved electrode 10, transponder 40 and system 80 discussed hereinabove and shown in FIGS. 2-4 and 6. Accordingly, the method begins at step 202 in which an RF signal is generated exterior to the cellular matter. At step 204, the RF signal is received by a transponder implanted within the cellular matter. The RF signal is adapted to power the transponder so that it can electrically interface with the cellular matter. At step 206, electrical signals generated by the cellular matter are detected by the powered transponder. The electrical signals generated by the cellular matter may originate from neural spike signals of peripheral neurons interfacing with the transponder. As discussed above, the ability to detect such spike signals is facilitated by powering the transponder via the RF signal. Thereafter, the method proceeds to step 208, whereby the RF signal is modulated in response to the detection of the electrical signal produced by the peripheral nerves. The modulation of the RF may be unique insofar as it may identify the nature of the signal generated by the cellular matter and/or indicate its origin. At step 210, the modulated RF signal is received and, thereafter, at step 212 the signal is analyzed to determine its ID characteristics. Thereafter, the modulated signal is processed to determine whether to generate additional RF signals to provide additional detection or stimulation of the peripheral nerves, whereby the method 200 returns to step 202.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An implantable medical device comprising:
 a body member comprising a biocompatible material;
 a wireless transponder enclosed by the body member; and
 grooves extending along the body member, wherein the grooves contain at least one electrode adapted to electrically interface the body member with the cellular matter growing along the body member.

2. The electrode of claim 1, wherein the biocompatible material is polymethylmethacrylate (PMMA), polydimethylsiloxane (PDMS), polytetrafluoroethylene (PTFE), parylene, polyurethane of polycarbonate and/or a combination thereof.

3. The electrode of claim 1, wherein the grooves extend along an outer portion of the body member.

4. The electrode of claim 1, wherein the grooves extend along an inner portion of the body member.

5. The electrode of claim 1, comprising electrode leads disposed along the recessed floor of the grooves, wherein the grooves are adapted to limit the growth of nerve fibers for electrically interfacing the electrodes.

6. The electrode of claim 5, wherein the electrode leads are formed of carbon nano-tubes.

7. The electrode of claim 1, comprising neurotrophic factors for promoting growth of peripheral nerves along the electrode.

8. The electrode of claim 1, wherein the length of the body member is less than two millimeters.

9. The electrode of claim 1, comprising wire leads extending from the body member, wherein the wire leads are adapted to electrically connect the body member to systems external to the body member.

10. A system for interfacing cellular matter, comprising:
 a grooved body member comprising a biocompatible material adapted to be coupled to a peripheral nerve; and
 a wireless transponder encased within the body member; wherein the wireless transponder is adapted to electrically interface via at least one electrode with the peripheral nerve.

11. The system of claim 10, comprising cellular matter grown along the outer portion of the body member.

12. The system of claim 10, comprising cellular matter grown along the inner portion of the body member.

13. The system of claim 10, comprising grooves extending along inner portions of the member or along outer portions of the body member.

14. The system of claim 13, comprising electrode leads disposed along the grooves.

15. The system of claim 14, wherein the electrode leads are formed of carbon nano-tubes.

16. The system of claim 10, comprising neurotrophic factors for promoting growth of peripheral nerves along the body member.

17. The system of claim 10, wherein the length of the body member is less than two millimeters.

18. The system of claim 10, wherein the transponder is powered by electromagnetic signals.

19. The system of claim 10, wherein the transponder comprises a microcoil with a core formed of a nano-crystalline magnetic alloy.

20. The system of claim 10, wherein the transponder comprises a sensor adapted for detecting neural spike signals.

21. The system of claim 20, wherein the sensor comprises a field effect transistor (FET).

* * * * *